United States Patent
Schmidt et al.

[11] Patent Number: 5,847,183
[45] Date of Patent: Dec. 8, 1998

[54] FATTY ALCOHOL (ETHER) SULFATES WITH IMPROVED LOW-TEMPERATURE BEHAVIOR

[75] Inventors: Wolfgang Schmidt, Monheim; Karl-Heinz Schmid, Mettmann; Michael Neuss, Cologne; Birgit Middelhauve, Monheim; Juan Carlos Wuhrmann, Duesseldorf; Dagmar Zaika, Mettmann, all of Germany

[73] Assignee: Henkel Corporation, Plymouth Mtg, Pa.

[21] Appl. No.: 746,783

[22] Filed: Nov. 15, 1996

[30] Foreign Application Priority Data

Nov. 15, 1995 [DE] Germany .................. 195 42 569.3

[51] Int. Cl.$^6$ .................................. C07C 303/28
[52] U.S. Cl. ................ 558/20; 558/31; 558/38; 558/41; 558/43
[58] Field of Search ................... 558/20, 31, 38, 558/41, 43

[56] References Cited

U.S. PATENT DOCUMENTS 3,413,331 11/1968 Beiser et al. .................. 260/458
5,446,188 8/1995 Gruber et al. .................. 558/42

OTHER PUBLICATIONS

Surfactants in Consumer Products, Springer Verlag, Berlin--Heidelberg, 1987, p. 61.

*Primary Examiner*—Johann Richter
*Assistant Examiner*—Jane C. Oswecki
*Attorney, Agent, or Firm*—Ernest G. Szoke; Wayne C. Jaeschke; Henry E. Millson, Jr.

[57] ABSTRACT

Fatty alcohol (ether) sulfates which are obtained by co-sulfating mixtures of (a) $C_{8-22}$ fatty alcohols and (b) $C_{8-22}$ fatty alcohol ethoxylates containing an average of 1.9 to 3.9 ethylene oxide units in a ratio by weight of 20:80 to 80:20, and then neutralizing the mixtures thus co-sulfated with aqueous bases. The substances have distinctly improved low-temperature behavior in relation to ether sulfates with comparable degrees of ethoxylation, and are useful as components of surface-active compositions.

26 Claims, No Drawings

FATTY ALCOHOL (ETHER) SULFATES WITH IMPROVED LOW-TEMPERATURE BEHAVIOR

BACKGROUND OF THE INVENTION

1. Field of the Invention

This invention relates to fatty alcohol (ether) sulfates with improved low-temperature behavior which are obtained by co-sulfation of alcohol/ethoxylate mixtures, to a process for their production and to the use of the ether sulfates for the production of surface-active formulations.

2. Statement of Related Art

Fatty alcohol ether sulfates are skin-compatible high-foaming anionic surfactants which are of particular importance for the production of liquid surface-active formulations, for example, manual dishwashing detergents or hair shampoos. Products obtained by sulfation of ethoxylated cocofatty alcohols with low degrees of ethoxylation are normally used for this purpose. They are generally prepared in the form of aqueous pastes with a solids content of 30 to 50% by weight which are still flowable at room temperature. However, both among raw material manufacturers and amound their customers, there is a demand for concentrated products with solids contents far above those of the commercially established ether sulfates, for example, to save water during storage and transport or to be able to make concentrates readily available. Although ether sulfates with a relatively high solids content can be directly produced by corresponding measures during neutralization of the products or at least dilute products can be subsequently concentrated, it has been found that known ether sulfates based on cocofatty alcohol with low degrees of ethoxylation crystallize at room temperature above a solids content of around 60% by weight and, hence, can no longer be pumped. Accordingly, the problem addressed by the present invention was to remedy this situation.

DESCRIPTION OF THE INVENTION

Other than in the operating examples, or where otherwise indicated, all numbers expressing quantities of ingredients or reaction conditions used herein are to be understood as modified in all instances by the term "about."

The present invention relates to fatty alcohol (ether) sulfates with improved low-temperature behavior which are obtained by co-sulfating mixtures of (a) at least one fatty alcohol corresponding to formula (I):

In which $R^1$ represents a linear or branched aliphatic alkyl radical containing 8 to 22 and preferably 12 to 18 carbon atoms, and (b) at least one fatty alcohol ethoxylate corresponding to formula (II):

In which $R^2$ represents a linear or branched aliphatic alkyl radical containing 8 to 22 and preferably 12 to 18 carbon atoms and n is an average number of 1.9 to 3.9, in a ratio by weight of 20:80 to 80:20, preferably 20:60 to 60:40 and, more preferably, 30:70 to 35:65, and neutralizing the mixtures thus co-sulfated with aqueous bases.

It has surprisingly been found that the fatty alcohol (ether) sulfates are still flowable and pumpable at 20° C. even when their solids content is well above 60% by weight. By contrast, ether sulfates of comparable chain length and degree of ethoxylation, which have been prepared by simple sulfation of a corresponding ethoxylate, are present as cutting-resistant crystallized pastes under the same conditions.

The present invention also relates to a process for the production of fatty alcohol (ether) sulfates with improved low-temperature behavior in which mixtures of (a) at least one fatty alcohol corresponding to formula (I):

In which $R^1$ represents a linear or branched aliphatic alkyl radical containing 8 to 22 and preferably 12 to 18 carbon atoms, and (b) at least one fatty alcohol ethoxylate corresponding to formula (II):

In which $R^2$ represents a linear or branched aliphatic alkyl radical containing 8 to 22 and preferably 12 to 18 carbon atoms and n is an average number of 1.9 to 3.9, in a ratio by weight of 20:80 to 80:20, preferably 20:60 to 60:40 and, more preferably, 30:70 to 35:65 are co-sulfated, and then neutralized with aqueous bases. The fatty alcohol (ether) sulfates produced by the above process are mixtures of fatty alcohol sulfate salts and fatty alcohol ether sulfate salts.

Fatty alcohols

Typical examples of fatty alcohols suitable for use as component (a) are caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and the technical mixtures thereof obtained, for example, in the high-pressure hydrogenation of technical methyl esters based on fats and oils or aldehydes from Roelen's oxosynthesis and as monomer fractions in the dimerization of unsaturated fatty alcohols. Technical fatty alcohols containing 12 to 18 carbon atoms, for example cocofatty alcohol, palm oil fatty alcohol, palm kernel oil fatty alcohol or tallow fatty alcohol, are preferred. Among the branched starting materials, alcohols commercially available as DOBANOL® and LIAL®, for example, are preferred.

Fatty alcohol ethoxylates

Fatty alcohol ethoxylates suitable for component (b) are addition products of 1.9 to 3.9 moles and preferably 2 to 3 moles of ethylene oxide with the fatty alcohols mentioned above. Fatty alcohol ethoxylates containing 12 to 18 carbon atoms in the fatty alkyl radical are preferably used. It has proved to be of particular advantage for the carbon chains of the fatty alcohols of component (a) and the ethoxylates of component (b) to be identical. The ethoxylates may have a conventional homolog distribution or a narrow homolog distribution.

Sulfation

The alcohol/ethoxylate mixtures may be sulfated by any of the known methods for sulfating fatty acid lower alkyl esters (cf. J. Falbe (ed.), "Surfactants in Consumer Products", Springer Verlag, Berlin-Heidelberg, 1987, page 61), preferably using reactors operating on the falling-film principle. Suitable sulfonating agents are chlorosulfonic acid and, in particular, gaseous sulfur trioxide. The sulfur trioxide is normally diluted with an inert gas, preferably air or nitrogen, and used in the form of a gas mixture containing the sulfonating agent in a concentration of 1 to 8% by volume and, more particularly, 2 to 5% by volume.

The molar ratio of alcohol/ethoxylate mixture to sulfating agent is normally from 1:0.95 to 1:1.3 and is preferably from 1:1 to 1:1.05. The sulfation reaction is normally carried out at temperatures of from 25° to 70° C. With regard to the viscosity of the starting materials on the one hand and the color quality of the resulting sulfation products on the other hand, it has proved to be optimal to carry out the reaction at a temperature in the range of from 30° to 55° C.

Neutralization

The acidic sulfation products accumulating during the sulfation reaction are stirred into aqueous bases, neutralized and adjusted to a pH value of from 6.5 to 8.5. Suitable neutralization bases are alkali metal hydroxides, such as sodium, potassium and lithium hydroxide, alkaline earth metal oxides and hydroxides, such as magnesium oxide, magnesium hydroxide, calcium oxide and calcium hydroxide, ammonia, mono-, di- and tri-$C_{2-4}$-alkanolamines, for example mono-, di- and triethanolamine, and primary, secondary or tertiary $C_{1-4}$ alkyl amines and glucamines. The neutralization bases are preferably used in the form of 5 to 55% by weight aqueous solutions, 25 to 50% by weight aqueous sodium hydroxide solutions being preferred.

In one preferred embodiment of the invention, neutralization is carried out in such a way that pastes with a solids content of from 60 to 80% by weight and, more particularly, from 65 to 75% by weight are formed.

Bleaching and Preservation

After neutralization, the sulfation products may be bleached in known manner by addition of hydrogen peroxide or sodium hypochlorite solution. 0.2 to 2% by weight of hydrogen peroxide, expressed as 100% substance, or corresponding quantities of sodium hypochlorite, based on the solids content of the solution of sulfation products, are used. The pH value of the solutions may be kept constant using suitable buffers, for example sodium phosphate or citric acid. Preservation, for example with formaldehyde solution, p-hydroxybenzoate, sorbic acid or other known preservatives, is advisable for stabilization against bacterial contamination.

Commercial Applications

The fatty alcohol (ether) sulfates according to the invention show advantageous low-temperature behavior, i.e. they are still flowable and pumpable even with solids contents above 65% by weight. Accordingly, they are suitable as raw materials for the production of numerous surface-active formulations such as, for example, liquid detergents, dishwashing detergents or hair shampoos, in which they may be present in quantities of from 1 to 50% by weight and preferably in quantities of from 5 to 25% by weight, based on the formulation.

EXAMPLES

Example 1

A mixture of 70 g (0.35 mole) of technical $C_{12/14}$ cocofatty alcohol (LOROL® Spezial, Henkel KGaA, Düsseldorf, FRG) and 187 g (0.65 mole) of $C_{12/14}$ cocofatty alcohol+2EO (DEHYDOL® LS2, Henkel KGaA) was introduced into and heated to 45° C. in a 1 liter sulfonation reactor equipped with a gas inlet pipe and a jacket cooling system. 84 g (1.05 mole) of gaseous sulfur trioxide (3% by volume in nitrogen), which had been driven out beforehand from a corresponding quantity of oleum, were introduced into the mixture over a period of 20 minutes. The crude sulfation product was neutralized together with 50% by weight sodium hydroxide solution. The resulting mixture of alkyl sulfate and ether sulfate sodium salts had a solids content of 70% by weight, the average degree of ethoxylation of the mixture being 1.2. The product had viscosities of 14,000 and 10,000 mPas (Brookfield RVF viscosimeter, 20 r.p.m., spindle 1) at 20° C. and 25° C., respectively, and was flowable and pumpable.

Examples 2 and 3

Example 1 was repeated using in Example 2, 60 g (0.3 mole) of cocofatty alcohol and 202 g (0.7 mole) of cocofatty alcohol+2EO and in Example 3, 80 g (0.4 mole) of cocofatty alcohol and 173 g (0.6 mole) of cocofatty alcohol+2EO. For solids contents of, again, 70% by weight, pastes flowable and pumpable at 20° C. were obtained in both cases.

Comparison Examples C1 and C2

As in Example 1, a) 1 mole of a $C_{12/14}$ cocofatty alcohol+1 EO adduct (Example C1) and b) 1 mole of a $C_{12/14}$ cocofatty alcohol+1.2EO adduct (Example C2) were sulfated with 1.05 mole of sulfur trioxide and neutralized with sodium hydroxide solution. The products were adjusted to a solids content of 70% by weight. However, both products were solid both at 20° C. and at 25° C.

What is claimed is:

1. A process for the production of aqueous fatty alcohol sulfate/fatty alcohol ether sulfate concentrates having improved low-temperature behavior comprising the steps of
   A) co-sulfating a mixture of
      (a) at lease one primary fatty alcohol corresponding to formula (I):

$$R^1OH \qquad (I)$$

In which $R^1$ represents a linear or branched aliphatic alkyl radical containing 8 to 22 carbon atoms, and
      (b) at least one primary fatty alcohol ethoxylate corresponding to formula (II):

$$R^2O(CH_2CH_2O)_nH \qquad (II)$$

in which $R^2$ represents a linear or branched aliphatic alkyl radical containing 8 to 22 carbon atoms, and n is an average number of 1.9 to 3.9, wherein the weight ratio of (a) to (b) is from about 20:80 to about 80:20; and
   B) neutralizing the co-sulfated mixture from step A) with an aqueous base.

2. The process of claim 1 wherein $R^1$ contains from 12 to 18 carbon atoms and $R^2$ contains from 12 to 18 carbon atoms.

3. The process of claim 1 wherein $R^1$ and $R^2$ are identical alkyl radicals.

4. The process of claim 1 wherein said weight ratio is from about 20:80 to about 60:40.

5. The process of claim 1 wherein said weight ratio is from about 30:70 to about 35:65.

6. The process of claim 1 wherein chlorosulfonic acid or gaseous sulfur trioxide is used as the sulfating agent.

7. The process of claim 6 wherein the sulfation reaction is carried out in a continuous reactor operating on the falling-film principle.

8. The process of claim 1 wherein the mixture in A) and the sulfating agent are present in a molar ratio of from about 1:0.95 to about 1:1.3.

9. The process of claim 8 wherein said molar ratio is from about 1:1 to about 1:1.05.

10. The process of claim 1 wherein in component A) (b), n is an average number of from 2 to 3.

11. The process of claim 1 wherein step A) is carried out at a temperature in the range of from about 25° to about 70° C.

12. The process of claim 11 wherein said temperature is from about 30° to about 55° C.

13. The process of claim 1 wherein step B) is carried out with from 5 to 55% by weight aqueous base selected from the group consisting of alkali metal hydroxides, alkaline earth metal oxides and hydroxides, ammonia, mono-, di- and tri-$C_{2-4}$-alkanolamines, primary, secondary and tertiary $C_{1-4}$ alkylamines, and glucamines.

14. The process of claim 1 wherein the neutralized mixture from step B) has a solids content of from about 60 to about 80% by weight.

15. The process of claim 14 wherein said solids content is from about 65 to about 75% by weight.

16. The process of claim 1 wherein the neutralized mixture from step B) has a pH in the range of from about 6.5 to about 8.5.

17. The process of claim 2 wherein $R^1$ and $R^2$ each contain from 12 to 18 carbon atoms, said weight ratio is from about 20:80 to about 60:40, and the sulfating agent is chlorosulfonic acid or gaseous sulfur trioxide.

18. The process of claim 17 wherein $R^1$ and $R^2$ are identical alkyl radicals, and said weight ratio is from about 30:70 to about 35:65.

19. The process of claim 17 wherein in component A) (b), n is an average number of from 2 to 3.

20. The process of claim 17 wherein step A) is carried out at a temperature in the range of from about 30° to about 55° C., and the mixture in A) and the sulfating agent are present in a molar ratio of from about 1:1 to about 1:1.05.

21. The process of claim 17 wherein the neutralized mixture from step B) has a solids content of from about 60 to about 80% by weight.

22. The aqueous concentrate produced by the process of claim 1.

23. The aqueous concentrate produced by the process of claim 17.

24. The aqueous concentrate produced by the process of claim 21.

25. In a surface-active formulation, the improvement wherein from about 1 to about 50% by weight of the aqueous concentrate of claim 22 is present therein.

26. In a surface-active formulation, the improvement wherein from about 5 to about 25% by weight of the aqueous concentrate of claim 22 is present therein.

* * * * *